United States Patent [19]
Quay et al.

[11] Patent Number: 5,798,266
[45] Date of Patent: Aug. 25, 1998

[54] METHODS AND KITS FOR OBTAINING AND ASSAYING MAMMARY FLUID SAMPLES FOR BREAST DISEASES, INCLUDING CANCER

[75] Inventors: Steven C. Quay; Debra L. Quay, both of Edmonds, Wash.

[73] Assignee: K-Quay Enterprises, LLC, Edmonds, Wash.

[21] Appl. No.: 709,207

[22] Filed: Aug. 27, 1996

[51] Int. Cl.$^6$ .................... G01N 33/48; G01N 33/53; G01N 33/567; G01N 33/542; A61M 1/06

[52] U.S. Cl. .................... 436/64; 435/6; 435/7.1; 435/7.2; 435/7.23; 435/7.9; 435/7.91; 435/7.92; 435/7.93; 435/7.94; 435/7.95; 435/29; 435/30; 435/296; 435/810; 435/975; 436/501; 436/523; 436/161; 436/162; 436/177; 436/178; 436/507; 436/508; 436/810; 436/813; 436/514; 604/74; 604/75; 604/76

[58] Field of Search .................... 435/6, 7.1, 7.2, 435/723, 7.9–7.95, 29, 30, 296, 810, 975; 436/501, 523–531, 64, 161, 162, 177, 178, 807, 808, 810, 813, 574–576; 604/74, 76

[56] References Cited

U.S. PATENT DOCUMENTS 5,007,899   4/1991   Larsson .................... 604/74

OTHER PUBLICATIONS

Rose, *Cancer Detection and Prevention* 16:43–51, 1992.
Cobo, *J. Perinat. Med* 21:77–85, 1993.
Vetvicka et al., *Biochemistry and Molecular Biology International* 30:921–928, 1993.
Rosen et al., *Cancer Investigation* 13:573–582, 1995.
North et al., *Breast Cancer Research and Treatment* 34: 229–235, 1995.
Porter–Jordan et al., *Breast Cancer* 8: 73–100, 1994.
Hayes, *Annals of Oncology* 4; 807–819, 1993.
Greiner, *Pharmaceutical Technology*, May 1993.
Sheahan et al., *A.J.C.P.* 94: 157–164, 1990.
Gordon et al., *Cancer Research* 50: 6229–6234, 1990.
Domagala et al., *American Journal of Pathology* 142:669–674, 1993.
Molinolo et al., *Cancer Research* 50: 1291–1298, 1990.
Ingelman–Sundberg et al., *Virchows Archiv A Pathol Anat* 415: 539–544, 1989.
Kawamoto, *Cancer* 73: 1836–1841, 1994.
Ceriani et al., *Breast Cancer Research and Treatment* 15: 161–174, 1990.
Nagle et al., *The Journal of Histochemistry and Cytochemistry* 34: 869–881, 1986.
Eskelinen et al., *Anticancer Research* 9: 437–440, 1989.
Eskelinen et al., *Anticancer Research* 8: 665–668, 1988.
Hou et al., *Radiology* 195: 568–569, 1995.
Roche, *Mayo Clinic Proc.* 69: 57–58, 1994.
Mori et al., *Jpn. J. Clin. Oncol.* 19: 373–379, 1989.
Inaji et al., *Cancer* 60: 3008–3013, 1987.
Rakhimberdiev, Izv. Akad. Nauk. Kaz. SSR Ser. Biol. vol. 4 p. 64 (and translation) 1980.
Physicians Desk Refrence, 49th Edition, p. 2193, 1995.
Fulkerson et al Aust. J. Biol. Sci. vol. 29 p. 357, 1976.
CA 93:215481 1980.

*Primary Examiner*—Sheela Huff
*Attorney, Agent, or Firm*—Townsend and Townsend and Crew

[57] ABSTRACT

Non-invasive methods and kits are provided for obtaining biological samples of mammary fluid or mammary fluid components by administering oxytocin or an oxytocin analogue to a mammalian patient to stimulate expression of mammary fluid. The oxytocin is preferably administered intranasally and causes myoepithelial contraction of target alveolar-ductal tissues of the breast. During or after mammary fluid expression, a biological sample is collected in the form of whole mammary fluid, whole cells or cellular components, other selected liquid or solid fractions of the mammary fluid, purified or bulk proteins, glycoproteins, peptides, nucleotides or other desired constituents of mammary fluid. Methods and kits are also provided for determining the presence or amount of a breast disease marker in biological samples of mammary fluid or mammary fluid components. Samples obtained according to the above sample collection methods are assayed to determine the presence and/or amount of a breast disease marker, for example a breast cancer marker such as CEA, HMFG, MCA, vasopressin, or cathepsin D, in the sample. Cellular samples obtained according to the above sample collection methods are also examined microscopically for cytological evidence of breast disease.

37 Claims, No Drawings

METHODS AND KITS FOR OBTAINING AND ASSAYING MAMMARY FLUID SAMPLES FOR BREAST DISEASES, INCLUDING CANCER

TECHNICAL FIELD

The invention relates to methods and kits for obtaining and assaying biological samples from mammary fluid. More specifically, the invention relates to methods and kits for obtaining and assaying fluid and cytological samples from the mammary glands of a mammalian subject for evaluating, diagnosing and managing breast disease, including infections, pre-cancerous conditions, cancer susceptibility and cancer.

BACKGROUND OF THE INVENTION

Breast cancer is by far the most common form of cancer in women, and is the second leading cause of cancer death in humans. Despite many recent advances in diagnosing and treating breast cancer, the prevalence of this disease has been steadily rising at a rate of about 1% per year since 1940. Today, the likelihood that a women living in North America will develop breast cancer during her lifetime is one in eight.

The current widespread use of mammography has resulted in improved detection of breast cancer. Nonetheless, the death rate due to breast cancer has remained unchanged at about 27 deaths per 100,000 women. All too often, breast cancer is discovered at a stage that is too far advanced, when therapeutic options and survival rates are severely limited. Accordingly, more sensitive and reliable methods are needed to detect small (less than 2 cm diameter), early stage, in situ carcinomas of the breast. Such methods should significantly improve breast cancer survival, as suggested by the successful employment of Papinicolou smears for early detection and treatment of cervical cancer.

In addition to the problem of early detection, there remain serious problems in distinguishing between malignant and benign breast disease, in staging known breast cancers, and in differentiating between different types of breast cancers (eg. estrogen dependent versus non-estrogen dependent tumors). Recent efforts to develop improved methods for breast cancer detection, staging and classification have focused on a promising array of so-called cancer "markers." Cancer markers are typically proteins that are uniquely expressed (eg. as a cell surface or secreted protein) by cancerous cells, or are expressed at measurably increased or decreased levels by cancerous cells compared to normal cells. Other cancer markers can include specific DNA or RNA sequences marking deleterious genetic changes or alterations in the patterns or levels of gene expression associated with particular forms of cancer.

A large number and variety of breast cancer markers have been identified to date, and many of these have been shown to have important value for determining prognostic and/or treatment-related variables. Prognostic variables are those variables that serve to predict disease outcome, such as the likelihood or timing of relapse or survival. Treatment-related variables predict the likelihood of success or failure of a given therapeutic plan. Certain breast cancer markers clearly serve both functions. For example, estrogen receptor levels are predictive of relapse and survival for breast cancer patients, independent of treatment, and are also predictive of responsiveness to endocrine therapy. Pertschuk et al., *Cancer* 66: 1663–1670, 1990; Parl and Posey, *Hum. Pathol.* 19: 960–966, 1988; Kinsel et al., *Cancer Res.* 49: 1052–1056, 1989; Anderson and Poulson *Cancer* 65: 1901–1908, 1989.

The utility of specific breast cancer markers for screening and diagnosis, staging and classification, monitoring and/or therapy purposes depends on the nature and activity of the marker in question. For general reviews of breast cancer markers, see Porter-Jordan et al., *Hematol. Oncol. Clin. North Amer.* 8: 73–100, 1994; and Greiner, *Pharmaceutical Tech.*, May, 1993, pp. 28–44. As reflected in these reviews, a primary focus for developing breast cancer markers has centered on the overlapping areas of tumorigenesis, tumor growth and cancer invasion. Tumorigenesis and tumor growth can be assessed using a variety of cell proliferation markers (for example Ki67, cyclin D1 and proliferating cell nuclear antigen (PCNA)), some of which may be important oncogenes as well. Tumor growth can also be evaluated using a variety of growth factor and hormone markers (for example estrogen, epidermal growth factor (EGF), erbB-2, transforming growth factor (TGF)α), which may be overexpressed, underexpressed or exhibit altered activity in cancer cells. By the same token, receptors of autocrine or exocrine growth factors and hormones (for example insulin growth factor (IGF) receptors, and EGF receptor) may also exhibit changes in expression or activity associated with tumor growth. Lastly, tumor growth is supported by angiogenesis involving the elaboration and growth of new blood vessels and the concomitant expression of angiogenic factors that can serve as markers for tumorigenesis and tumor growth.

In addition to tumorigenic, proliferation and growth markers, a number of markers have been identified that can serve as indicators of invasiveness and/or metastatic potential in a population of cancer cells. These markers generally reflect altered interactions between cancer cells and their surrounding microenvironment. For example, when cancer cells invade or metastasize, detectable changes may occur in the expression or activity of cell adhesion or motility factors, examples of which include the cancer markers Cathepsin D, plasminogen activators, collagenases and other factors. In addition, decreased expression or overexpression of several putative tumor "suppressor" genes (for example nm23, p53 and rb) has been directly associated with increased metastatic potential or deregulation of growth predictive of poor disease outcome.

In summary, the evaluation of proliferation markers, oncogenes, growth factors and growth factor receptors, angiogenic factors, proteases, adhesion factors and tumor suppressor genes, among other cancer markers, can provide important information concerning the risk, presence, status or future behavior of cancer in a patient. Determining the presence or level of expression or activity of one or more of these cancer markers can aid in the differential diagnosis of patients with uncertain clinical abnormalities, for example by distinguishing malignant from benign abnormalities. Furthermore, in patients presenting with established malignancy, cancer markers can be useful to predict the risk of future relapse, or the likelihood of response in a particular patient to a selected therapeutic course. Even more specific information can be obtained by analyzing highly specific cancer markers, or combinations of markers, which may predict responsiveness of a patient to specific drugs or treatment options.

Methods for detecting and measuring cancer markers have been recently revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modern immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining breast tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art which allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of breast cancer evaluation, the use of conventional or needle biopsy samples for cancer marker assays is often undesirable, because a primary goal of such assays is to detect the cancer before it progresses to a palpable or mammographically detectable tumor stage. Prior to this stage, biopsies are generally contraindicated, making early screening and low risk monitoring procedures employing such samples untenable. Therefore, there is general need in the art to obtain samples for breast cancer marker assays by less invasive means than biopsy, for example by serum withdrawal.

Efforts to utilize serum samples for breast cancer marker assays have met with limited success, largely because the targeted markers are either not detectable in serum, or because telltale changes in the levels or activity of the markers cannot be monitored in serum. In addition, the presence of breast cancer markers in serum probably occurs at the time of micro-metastasis, making serum assays less useful for detecting pre-metastatic disease. In contrast, fluid within the mammary glands themselves is expected to contain much higher and more biologically relevant levels of breast cancer markers than serum, particularly in view of the fact that 80%–90% of all breast cancers occur within the intraductal epithelium of these glands. Fluid within the breast ducts is expected to contain an assemblage and concentration of hormones, growth factors and other potential markers comparable to those secreted by, or acting upon, the surrounding cells of the alveolar-ductal system. Likewise, mammary fluid is expected to contain cells and solid cellular debris or products that can be used in cytological or immunological assays to evaluate intracellular or cell surface markers that may not be detectable in the liquid fraction of mammary fluid.

Previous attempts to develop non-invasive breast cancer marker assays utilizing mammary fluid samples have included studies of mammary fluid obtained from patients presenting with spontaneous nipple discharge. In one of these studies, conducted by Inaji et al., Cancer 60: 3008–3013, 1987, levels of the breast cancer marker carcinoembryonic antigen (CEA) were measured using conventional, enzyme linked immunoassay (ELISA) and sandwich-type, monoclonal immunoassay methods. These methods successfully and reproducibly demonstrated that CEA levels in spontaneously discharged mammary fluid provide a sensitive indicator of nonpalpable breast cancer. In a subsequent study, also by Inaji et al., Jpn. J. Clin. Oncol. 19: 373–379, 1989, these results were expanded using a more sensitive, dry chemistry, dot-immunobinding assay for CEA determination. This latter study reported that elevated CEA levels occurred in 43% of patients tested with palpable breast tumors, and in 73% of patients tested with nonpalpable breast tumors. CEA levels in the discharged mammary fluid were highly correlated with intratumoral CEA levels, indicating that the level of CEA expression by breast cancer cells is closely reflected in the mammary fluid CEA content. Based on these results, the authors concluded that immunoassays for CEA in spontaneously discharged mammary fluid are useful for screening nonpalpable breast cancer.

Although the evaluation of mammary fluid has been shown to be a useful method for screening nonpalpable breast cancer in women who experience spontaneous nipple discharge, the rarity of this condition renders the methods of Inaji et al. inapplicable to the majority of women who are candidates for early breast cancer screening. In addition, the first Inaji report cited above determined that certain patients suffering spontaneous nipple discharge secrete less than 10 µl of mammary fluid, which is a critically low level for the ELISA and sandwich immunoassays employed in that study. It is likely that other antibodies used to assay other cancer markers may exhibit even lower sensitivity than the anti-CEA antibodies used by Inaji and coworkers, and may therefore not be adaptable or sensitive enough to be employed even in dry chemical immunoassays of small samples of spontaneously discharged mammary fluid.

In view of the above, an important need exists in the art for more widely applicable, non-invasive methods and materials to obtain biological samples for use in evaluating, diagnosing and managing breast disease including cancer, particularly for screening early stage, nonpalpable breast tumors. A related need exists for methods and materials that utilize such readily obtained biological samples to evaluate, diagnose and manage breast disease, particularly by detecting or measuring selected breast cancer markers, or panels of breast cancer markers, to provide highly specific, cancer prognostic and/or treatment-related information, and to diagnose and manage pre-cancerous conditions, cancer susceptibility, breast infections and other breast diseases.

SUMMARY OF THE INVENTION

It is therefore an object of the present invention to provide non-invasive methods and kits for obtaining biological samples that can be employed in assays for evaluating, diagnosing and managing breast disease, particularly cancer.

It is a further object of the invention to achieve the above object in assay methods and kits that are widely applicable to a broad range of patients, and that include useful assays and kits for screening early stage, nonpalpable mammary tumors.

It is yet another object of the invention to provide methods and kits that utilize the aforementioned biological samples to evaluate, diagnose and manage breast disease, preferably breast cancer, by detecting and/or measuring selected breast disease markers such as breast cancer markers, or panels of breast cancer markers, to provide highly specific prognostic and/or treatment-related information to the clinician.

The invention achieves these objects and other objects and advantages that will become apparent from the description which follows by providing non-invasive methods for obtaining biological samples from a mammary organ of a mammalian patient. Specifically, the methods of the invention involve administering oxytocin or an oxytocin analog to a mammalian patient in an amount that is effective to stimulate expression of mammary fluid from a nipple of the patient. The oxytocin is preferably administered intranasally and is allowed to reach a target alveolar-ductal tissue of the breast where the oxytocin stimulates myoepithelial contraction of the alveolar-ductal tissue. Alternatively, an intramuscular or intravascular injection of oxytocin can effect the same myoepithelial contraction response as the intranasal administration route. A mammary fluid collector, preferably a breast pump, is then applied to the nipple and is used to receive the expressed breast fluid. In preferred methods involving use of a breast pump, negative pressure is generated on the breast to facilitate the oxytocin stimulated expression of mammary fluid. Alternatively, the mammary fluid can be expressed and collected without the aid of a breast pump, which may require an increase of oxytocin dosage or lengthening of the post administration time period before breast fluid is fully expressed from the nipple. During or after the mammary fluid expression step, a biological sample is collected from the expressed mammary fluid, which sample may consist of whole mammary fluid, whole cells, cell fragments, cell membranes, selected liquid, cellular or other solid fractions of the mammary fluid, as well as proteins, glycoproteins, peptides, nucleotides (including DNA and RNA polynucleotides) and other like biochemical and molecular constituents of the mammary fluid.

In related aspects of the invention, methods are provided for determining the presence or amount of a breast disease marker, preferably a breast cancer marker, in biological samples obtained from a mammary organ of a mammalian patient. These methods involve intranasal, intramuscular or intravascular administration of oxytocin or an oxytocin analog to mammalian patients in amounts effective to stimulate mammary fluid expression in the patient. Once a sufficient post-administration time period has elapsed to allow the oxytocin to reach and stimulate target alveolar-ductal tissues, mammary fluid is collected directly from the nipple or, alternatively, the breast is pumped, and a biological sample from expressed mammary fluid is collected, as above. After the sample is collected a bioassay is conducted on the sample to determine the presence and/or amount of the breast disease marker in the sample. Suitable bioassays in this regard include assays to detect known markers of breast infection, such as assays employing immunological or other suitable probes to detect specific antigens and other markers expressed by selected pathogens, including bacterial and viral pathogens. More preferred bioassays will detect individual markers or panels of markers of benign breast tumors, pre-cancerous breast disease, and/or breast cancer, such as assays employing immunological or other suitable probes to detect specific antigens and other markers expressed by benign, pre-cancerous and/or cancerous alveolar-ductal cells of the breast.

In yet additional aspects of the invention, clinically useful kits are provided for determining the presence and/or amount of a breast disease marker, preferably a breast cancer marker, in biological samples obtained from a mammary organ of a mammalian patient. The kits include a pharmaceutical preparation of oxytocin in a biologically suitable carrier. Preferably, the oxytocin preparation is a solution of oxytocin provided in an intranasal spray applicator. The kits also preferably include a collecting device for collecting a biological sample from the expressed mammary fluid, which collecting device may range from a simple fluid reservoir to solid phase media that can be directly incorporated into solid phase bioassays. In this context, an optional breast pump may also be provided serving a dual purpose of applying negative pressure to the breast to facilitate mammary fluid expression from the nipple following oxytocin stimulation, and to provide a reservoir or solid phase collecting device incorporated within the breast pump for biological sample collection. In particularly preferred embodiments of the invention, kits include compositions and/or devices for detecting the presence or amount of a breast disease marker in the biological sample, for example an immunological or molecular probe that binds or reacts with a breast cancer marker.

DETAILED DESCRIPTION OF THE INVENTION

As noted above, the invention provides methods for obtaining biological samples from mammary fluid. Preferably, these methods are non-invasive, meaning they are non-surgical and do not involve penetration of the breast by needles or other intrusive devices. To achieve a non-invasive sample collecting method, the invention relies specifically on administering the peptide hormone oxytocin to a mammalian patient, in an amount that is effective to stimulate expression of mammary fluid from a nipple of the patient when a breast pump is applied to the nipple to assist the mammary fluid expression. Preferably the oxytocin preparation is administered intranasally and is administered in an amount that is intranasally effective to stimulate expression of mammary fluid from the nipple.

Oxytocin is a peptide hormone of pituitary origin which is naturally released into the bloodstream of lactating women in response to suckling, and stimulates contraction of myoepithelial cells in the mammary alveoli and ducts to cause milk ejection. Cobo. *J. Perinat. Med.* 21: 77–85, 1993. The drug has also been widely used for stimulating labor in pregnant women, due to its activity of stimulating uterine contractions. Satin et al., *Am. J. Obstet. Gynecol.* 166: 1260–1261, 1992. For these reasons, the pharmacology of oxytocin has been thoroughly investigated, including detailed studies of effective dosages, half-life and potential side effects.

For use in the present invention, an oxytocin preparation is provided for intranasal, intramuscular, or intravenous administration that contains oxytocin in a biologically suitable, liquid carrier. The most economic oxytocin preparations utilize a synthetic oxytocin analogue (eg. Pitocin® or Syntocinon®) available from various providers, for example Sandoz (Basel, Switzerland) and United States Pharmacopeia. Naturally occuring oxytocin from mammalian sources is of course suitable, as are other known, naturally occuring oxytocin-like peptide analogues and their synthetic counterparts having similar activities for stimulating alveolar-ductal myoepithelial contraction. (See for example, Amico et al., *J. Clin. Endocrinol. Metab.* 60: 5, 1985, incorporated herein by reference in its entirety).

For use in the methods and kits of the invention, a preferred oxytocin preparation contains approximately 40 USP units of oxytocin per ml of liquid carrier. Preferred liquid carriers are biologically compatible solutions, such as a lactated Ringer's solution or other physiologically balanced, sterile, non-toxic and non-irritative solutions. To administer the oxytocin intranasally, a standard nasal squeeze bottle is used, which delivers approximately 0.5 ml of the oxytocin preparation into the patient's nostril when squeezed. The oxytocin is absorbed by the nasal mucosa into the systemic circulation where it reaches and acts specifically on the myoepithelial cells surrounding the alveoli of the breast and making up the walls of the lactiferous ducts, causing their smooth muscle fibers to contract and force any fluids present into the large ducts or sinuses where it can be expressed from the nipple spontaneously onto a sample collector or by the further action of a breast pump. Intranasal application of the spray preparation is therefore a practical and effective method of administration. The half-life of oxytocin in the human bloodstream is extremely short, estimated to be about 10–15 minutes or less, due to its rapid removal from plasma by the kidney, liver, and mammary gland, and the time to pharmacokinetic and clinical steady state is readily determined depending on the mode of administration (eg. bolus dosage, repeat administration, or steady infusion). (See for example, Gonser, *Arch. Gynecol. Obstet.* 256: 63–66, 1995; and Orhue, *Obstet. Gynecol.* 83: 229–233, 1994, each incorporated herein by reference in its entirety). It is therefore a routine matter to determine an appropriate concentration and dose of the oxytocin preparation to administer an effective amount (either intranasally effective, intravenously effective, or intramuscularly effective) of the oxytocin to cause expression of mammary fluid with or without the assistance of a breast pump. (See for example, Newton, *Ann. N.Y. Acad. Sci.* 652: 481–483; Mena, *Neuroendocrinology* 61: 722–730, 1995; Gonser, *Arch. Gynecol. Obstet.* 256: 63–66, 1995; Orhue, *Obstet. Gynecol.* 83: 229–233, 1994; Satin et al., *Am. J. Obstet. Gynecol.*, 166: 1260–1261, 1992; and Satin et al., *Obstet. Gynecol.* 83: 234–238, 1994, each incorporated herein by reference in its entirety).

Although not all female patients are expected to be responsive to intranasal oxytocin stimulation, an intranasally effective amount of oxytocin for the purposes of the invention can be readily determined. As used herein, an intranasally effective amount of oxytocin is an amount of oxytocin sufficient to intranasally stimulate the expression of at least 3 µl of mammary fluid in at least 50% of non-lactating female patients with the aid of negative pressure to the nipple of between 50–200 mm Hg applied by a breast pump up to 45 min after a first administration of the oxytocin spray. It may be necessary, and indeed preferred, to administer a low, preliminary dose of oxytocin to the patient, for example a single spray of a 40 Unit/ml oxytocin solution in each nostril, or multiple sprays of a lower concentration oxytocin preparation, and thereafter wait to determine a particular patient's sensitivity. If there is no reaction with an initial application of the breast pump after a short post-administration period of 2–15 minutes, and preferably 2–5 minutes, a booster dose of the oxytocin spray may be administered and the pump reapplied. In this way, the clinician can modulate the dosage to each patient's varying sensitivity, and thereby minimize potential adverse side effects. Alternatively, intramuscular or intravenous ocytocin administration can be used according to the same dosage determination and administration principles in patients where intranasal administration fails or is otherwise contraindicated as a preferred mode of administration.

Once an intranasally effective dose of the oxytocin is administered and the clinician has allowed a suitable post-administration period to elapse for the oxytocin to reach and stimulate the target alveolar-ductal tissue, the breast pump is applied according to well known procedures and negative pressure is generated on the breast to facilitate the expression of mammary fluid. Within the methods of the invention, negative pressures of 50–200 mm Hg are preferred, and these pressures are maintained, preferably intermittently, for approximately 1–15 minutes, depending on the sensitivity of individual patients, oxytocin dosage and other factors. Alternatively, mammary fluid expression can be achieved without the aid of a breast pump using a simple collector to receive the expressed breast fluid, as described herein.

The volume of expressed mammary fluid will vary depending on a variety of factors, including patient sensitivity to oxytocin, dosage of oxytocin delivered, time and pressure of breast pump administration, and other factors. For the least sensitive breast marker assays of the invention, a volume of expressed mammary fluid of 300–500 µl is preferred to provide ample material for conducting the assay, and these volumes will be obtainable from a substantial proportion of women treated according to the above methods. To express 300–500 µl of mammary fluid, some women will require repeated stimulation treatments, perhaps requiring pooling of mammary fluid samples obtained during multiple patient visits. However, for more sensitive assays of the invention, eg. solid phase immunoassays, much smaller samples of 3 µl or less will be suitable to carry out the assays, particularly in the case of breast cancer markers that are naturally secreted into the mammary fluid and are therefore expected to be present in very high concentrations compared to, for example, breast epithelial cell surface antigens or intracellular antigens that are not secreted.

During or after the mammary fluid expression step, a biological sample is collected from the expressed mammary fluid. A range of suitable biological samples are contemplated and will be useful within the methods of the invention, including whole mammary fluid, selected liquid or solid fractions of the mammary fluid, whole cells or cellular constituents, proteins, glycoproteins, peptides, nucleotides (including DNA and RNA polynucleotides) and other like biochemical and molecular constituents of the mammary fluid. Sample collection can be achieved simply by receiving the expressed mammary fluid within a suitable reservoir, such as an ordinary sample storage container or assay vessel. Alternatively, samples can be collected by exposing the expressed mammary fluid to conventional buffers, diluents, extraction or chromatographic media, filters, etc., to stabilize or prepare the sample for further processing or direct incorporation into a desired assay. In preferred embodiments of the invention, the expressed mammary fluid is exposed to a solid phase medium, such as a microscopic glass slide, nitrocellulose filter, affinity column, dot blot matrix or other like medium, that will selectively adsorb, bind, filter or otherwise process desired components of the mammary fluid, such as bulk or selected proteins, for convenient incorporation into a desired assay. The range of contemplated sample collection procedures and materials that are useful within the invention is broad, and selected methods and materials will vary with each selected assay, as will be understood and readily practiced by those skilled in the art.

Although a fundamental utility of the present invention lies in the novel, non-invasive methods for obtaining biological samples from mammary fluid, additional methods are disclosed herein that provide useful assays for detecting and/or measuring important breast disease markers in these samples. In this context, the invention provides a broad range of assay methods incorporating known procedures and reagents for determining the presence and/or expression levels of breast disease markers, particularly breast cancer markers, in biological samples. As incorporated within the invention, these methods involve administration of oxytocin to mammalian patients, preferably via intranasal administration, in amounts effective to stimulate mammary fluid expression in the patient, as described above. Once a sufficient post-administration time period has elapsed to allow the oxytocin to reach and stimulate target alveolar-ductal tissues, the breast is pumped and a biological sample is collected, as described above. After the sample is collected, a bioassay is conducted on the sample to determine the presence and/or amount of a selected breast disease marker, preferably a breast cancer marker or panel of breast cancer markers, in the sample.

As used herein, the term breast disease marker refers to any cell, cell fragment, protein, peptide, glycoprotein, lipid, glycolipid, proteolipid, or other molecular or biological material that is uniquely expressed (eg. as a cell surface or secreted protein) by diseased breast cells, or is expressed at a statistically significant, measurably increased or decreased level by diseased breast cells, or in association with breast disease (eg. a protein expressed by an infectious agent associated with breast disease), or is expressed at a statistically significant, measurably increased or decreased level by diseased breast cells compared to normal breast cells, or which is expressed by non-diseased breast cells in association with breast disease (eg. in response to the presence of diseased breast cells or substances produced therefrom). Breast disease markers can also include specific DNA or RNA sequences marking a deleterious genetic change, or an alteration in patterns or levels of gene expression significantly associated with breast disease. Preferred breast disease markers include markers of breast infections, benign neoplasia, malignant neoplasia, pre-cancerous conditions, and conditions associated with an increased risk of cancer.

As used herein, the term breast cancer marker refers to a subset of breast disease markers, namely any protein, peptide, glycoprotein, lipid, glycolipid, proteolipid, or other molecular or biological material that is uniquely expressed (eg. as a cell surface or secreted protein) by cancerous cells, or is expressed at a statistically significant, measurably increased or decreased level by cancerous cells compared to normal cells, or which is expressed by non-cancerous cells in association with cancer (eg. in response to the presence of cancerous cells or substances produced therefrom). Breast cancer markers can also include specific DNA or RNA sequences marking a deleterious genetic change, or an alteration in patterns or levels of gene expression significantly associated with cancer. In addition, breast cancer markers can include cytological features of whole cells present in mammary fluid, such as nuclear inclusions or cytoplasmic structures or staining attributes uniquely expressed by, or associated with, cancerous cells.

Among the breast cancer markers that are useful within the methods of the invention, a subset are described in representative review articles by Porter-Jordan et al., *Hematol. Oncol. Clin. North Amer.* 8: 73–100, 1994; and Greiner, *Pharmaceutical Tech,* May, 1993, pp. 28–44, each incorporated herein by reference in its entirety. Other suitable markers are also widely known and can be readily incorporated into the methods of the invention using information and methods generally known or available in the literature. Preferred breast cancer markers for use within the invention include well characterized markers that have been shown to have important value for determining prognostic and/or treatment-related variables in human female patients. As noted previously, prognostic variables are those variables that serve to predict outcome of disease, such as the likelihood or timing of relapse or survival. Treatment-related variables predict the likelihood of success or failure of a given therapeutic program. Determining the presence or level of expression or activity of one or more of these markers can aid in the differential diagnosis of patients with malignant and benign abnormalities, and can be useful for predicting the risk of future relapse or the likelihood of response to a selected therapeutic option.

It is important to note, however, that the invention does not rely solely on breast disease markers that meet the stringent requirements of sensitivity and specificity that would render the marker immediately acceptable for clinical application to human patients. On the contrary, a number of breast disease markers contemplated within the invention fall short of these stringent criteria, and nonetheless provide useful information that can be of substantial benefit in detecting, differentially diagnosing or managing breast cancer. Such non-clinically accepted markers are useful for immediate application within the methods of the invention as basic research tools, and as adjunctive tools in clinical applications. Beyond these immediate applications, many such markers are expected to be further developed and refined according to the methods of the invention to the point of direct clinical applicability, particularly in assay methods that analyze combinations of markers to generate complementary data of greater predictive value than data yielded by individual markers alone.

The preferred assay methods of the invention particularly focus on breast cancer markers associated with tumorigenesis, tumor growth, neovascularization and cancer invasion, and which by virtue of this association provide important information concerning the risk, presence, status or future behavior of cancer in a patient. As noted previously, tumorigenesis and tumor growth can be assessed using a variety of cell proliferation markers (for example Ki67, cyclin D1 and PCNA). Tumor growth can also be evaluated using a variety of growth factor and hormone markers (for example estrogen, EGF, erbB-2, and TGFα), receptors of autocrine or exocrine growth factors and hormones (for example IGF and EGF receptors), or angiogenic factors. In addition to tumorigenic, proliferation and growth markers, a number of markers provide information concerning cancer invasion or metastatic potential in cancer cells, for example by indicating changes in the expression or activity of cell adhesion or motility factors. Exemplary markers in this context include Cathepsin D, plasminogen activators and collagenases. In addition, expression levels of several putative tumor "suppressor" genes, including nm23, p53 and rb, provide important data concerning metastatic potential, or growth regulation of cancer cells. A large number and variety of suitable breast cancer markers in each of these classes have been identified, and many of these have been shown to have important value for determining prognostic and/or treatment-related variables relating to breast cancer.

Prior to or concurrent with each assay run of the invention, it is preferable to perform a preliminary evaluation to verify sample origin and/or quality. The focus of such preliminary evaluations is to verify that the sample collected from expressed mammary fluid is indeed of mammary origin, and is not contaminated with other potential contaminants, such as sweat from skin surrounding the nipple. For these sample verification purposes, a variety of assays are available which identify mammary fluid markers known to be present in mammalian mammary fluid, and which are preferably highly specific markers for mammary fluid (i.e. markers which are typically always present in mammary fluid and which are absent from all, or most of, other potentially contaminating bodily fluids and tissues). However, an acceptable level of specificity for mammary fluid markers within the methods of the invention is provided by markers that are simply known to be present in mammary fluid, even though they may be present in other bodily fluids. One such marker is the enzyme lysozyme, which is a normal component of human serum, urine, saliva, tears, nasal secretions, vaginal secretions, seminal fluid, and mammary fluid. Lysozyme (muramidase) is an enzyme which hydrolyzes beta 1,4-glycosidic linkages in the mucopolysaccharide cell wall of a variety of microorganisms resulting in cell lysis. Quantitative measurement of lysozyme is readily accomplished by a well known agar plate diffusion method, described in detail in the instructions provided with the Quantiplate® lysozyme test kit, available from Kallestad, Sanofi Diagnostics (Chasta, Minn.), incorporated herein by reference in its entirety.

Other mammary fluid markers for sample verification that are more specific than lysozyme are preferred within the methods of the invention, and can be readily incorporated within the invention based on published and generally known information. The most preferred among these markers are proteins and other biological substances that are specifically expressed or enriched in mammary fluid. A diverse array of suitable markers in this context have been characterized and have already been used to develop specific antibodies, including affinity purified and monoclonal antibodies. These antibodies can in turn be employed as immunological probes to determine the presence or absence, and/or to quantify, selected mammary fluid markers to verify mammary fluid sample origin and quality. Mammary fluid markers of particular interest for use within the invention include specific cytokeratins that are characteristically expressed by normal and cancerous mammary epithelial cells, against which specific panels of antibody probes have already been developed. (See for example, Nagle, *J. Histochem. Cytochem.* 34: 869–881, 1986, incorporated herein by reference in its entirety). Also useful as mammary fluid markers are the human mammary epithelial antigens (HME-Ags) corresponding to glycoprotein components of the human milk fat globulin (HMFG) protein, against which specific antibodies (eg anti HMFG1, Unipath, U.K.) are also available. (see Rosner et al., *Cancer Invest.* 13: 573–582, 1995; Ceriani et al. *Proc. Natl. Acad. Sci. USA* 74: 582–586, 1982; Ceriani et al., *Breast Cancer Res. Treat.* 15; 161–174, 1990, each incorporated herein by reference in its entirety).

To conduct the breast disease marker assays provided within the invention, a collected biological sample from mammary fluid is generally exposed to a probe that specifically binds to a selected breast disease or breast cancer marker, or otherwise interacts with the marker in a detectable manner to indicate the presence or absence, or amount, of the breast disease or breast cancer marker in the sample. Selected probes for this purpose will generally depend on the characteristics of the breast disease marker, i.e. on whether the marker is a protein polynucleotide or other substance. In preferred embodiments of the invention, the breast disease marker is a protein, peptide or glycoprotein, all of which are effectively targeted in breast disease marker assays using specific immunological probes. These immunological probes can be labeled with a covalently bound label to provide a signal for detecting the probe, or can be indirectly labeled, for example by a labeled secondary antibody that binds the immunological probe to provide a detectable signal.

General methods for the production of non-human antisera or monoclonal antibodies (e.g., murine, lagormorpha, porcine, equine) are well known and may be accomplished by, for example, immunizing an animal with a selected breast disease marker protein, peptides synthesized to include part of the marker protein sequence, degradation products including part of the marker protein sequence, or fusion proteins including all or part of the marker protein linked to a heterologous protein or peptide. Within various embodiments, monoclonal antibody producing cells are obtained from immunized animals, immortalized and screened, or screened first for the production of an antibody that binds to the selected breast cancer marker protein or peptide, and then immortalized. It may be desirable to transfer the antigen binding regions (i.e., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397 (incorporated herein by reference in its entirety). Alternatively, a human monoclonal antibody or portions thereof may be identified by first screening a human B-cell cDNA library for DNA molecules that encode antibodies that specifically bind to the selected breast disease marker according to the method generally set forth by Huse et al. (*Science* 246: 1275–1281, 1989 (incorporated herein by reference in its entirety). The DNA molecule may then be cloned and amplified to obtain sequences that encode the antibody (or binding domain) of the desired specificity.

Also contemplated within the invention are bifunctional antibodies having independent antigen binding sites on each immunoglobulin molecule (as disclosed for example in *Thromb. Res. Suppl. X:* 83, 1990, and in *The Second Annual IBC International Conference on Antibody Engineering*, A. George ed., Dec. 16–18, 1991; each incorporated herein by reference in its entirety), as well as panels of individual antibodies having differing specificities. Bifunctional antibodies and antibody panels of particular use within the invention include antibodies and panels of antibodies that bind to two or more selected breast disease markers to generate complementary data of greater predictive value than data yielded by individual markers alone.

Monoclonal antibodies are particularly useful within the invention as labeled probes to detect, image and/or quantify the presence or activity of selected breast disease markers. In this context, monoclonal antibodies that specifically bind to selected breast disease markers are provided which incorporate one or more well known labels, such as a dye, fluorescent tag or radiolabel. By incorporating such a label, the antibodies can be employed in routine assays to determine expression, localization and/or activity of one or more selected breast disease markers in a biological sample including, or derived from, mammary fluid. Results of these assays to determine expression, localization and/or activity of a selected breast disease marker in a test sample taken from a patient at risk for breast disease, or known to have breast disease, can be compared to results from control studies detecting and/or quantifying the same marker in biological samples obtained from normal patients negative for breast disease. In this manner, baseline data and cutoff values can be determined according to routine methods to refine the assays of the invention and adapt them for direct clinical application.

Detection and/or quantification of breast disease markers in the biological samples of the invention can be accomplished using a variety of methods. Preferred methods in this regard include well known ELISA immunoassays, immunoprecipitation assays, and various solid phase immunoassays including Western blotting, dot blotting and affinity purification immunoassays, among other methods. Comparable methods are disclosed herein, or are elsewhere disclosed and known in the art, for using non-antibody probes to detect and/or quantify the expression and/or activity of breast disease markers. Suitable non-antibody probes for use within the invention include, for example, labeled nucleotide probes that hybridize at standard or high stringency to DNA transcripts of oncogenes and other DNA sequences associated with elevated breast disease risk, or with mRNA transcripts encoding breast disease marker proteins. Other suitable probes include labeled ligands, binding partners and co-factors of breast disease markers (eg. growth factor receptor ligands, or substrates of breast cancer associated proteases such as cathepsin D). In certain preferred embodiments of the invention, cDNA and oligonucleotide probes are employed in Northern, Southern and dot-blot assays for identifying and quantifying the level of expression of a selected breast disease marker in cell samples collected from expressed mammary fluid. Measuring the level of expression of breast disease markers according to these methods will provide important prognostic and treatment-related information for assessing a broad range of breast disease, including the genesis, growth and invasiveness of cancer, in mammals, particularly humans. For example, assays utilizing oligonucleotide probes will assist early screening to evaluate heritable genetic lesions associated with breast cancer, and to distinguish between pre-cancerous, early cancerous and likely metastatic lesions in patients.

In addition to the above mentioned sample collection and assay methods, the invention also provides kits and multicontainer units comprising reagents and components for practicing the sample collection and assay methods of the invention. Briefly, these kits include basic components for obtaining a biological sample from mammary fluid, including a pharmaceutical preparation of oxytocin in a biologically suitable carrier. Preferably, the oxytocin preparation is provided in an intranasal spray applicator and contains approximately 40 USP units of oxytocin per ml of liquid carrier, which carrier is a simple, inexpensive buffered saline solution. Preferred applicators can be in any of a variety of pressurized aerosol or hand-pump reservoir forms, with a nozzle for directing a liquid spray of the oxytocin into a patient's nostril. The kits also preferably include a collecting device for collecting a biological sample from the expressed mammary fluid, which collecting device may range from a simple fluid reservoir to solid phase media that can be directly incorporated into solid phase bioassays. In this context, an optional breast pump may also be provided that is applicable to a human breast and designed to generate intermittent or sustained negative pressures in an area surrounding the nipple of between about 50–200 mm Hg. More preferably, the breast pump serves a dual purpose of applying negative pressure to the breast to facilitate mammary fluid expression from the nipple following oxytocin stimulation, and to provide a reservoir or solid phase collecting device incorporated within the breast pump for biological sample collection.

Kits for practicing the assay methods of the invention include a suitable container or other device for collecting a biological sample from expressed mammary fluid. A range of suitable collection devices are contemplated corresponding to a wide range of suitable biological samples that may be collected from the expressed mammary fluid. For example, simple sterile containers or reservoirs are provided to collect whole mammary fluid. Alternatively, a variety of solid phase devices, including microscopic glass slides, membranes, filters, beads and like media, are provided to receive or partition selected liquid or solid fractions of the mammary fluid, to receive or partition cells or cellular constituents from the mammary fluid, or to receive or partition purified or bulk proteins, glycoproteins, peptides, nucleotides (including DNA and RNA polynucleotides) or other like biochemical and molecular constituents from the mammary fluid. A wide variety of such sample collection devices are disclosed herein, or are otherwise widely known or described in the literature, which can be readily adapted for use within specific embodiments of the invention. These collection devices may be provided as a component of the breast pump (such as a removable fluid reservoir or nitrocellulose filter placed within the pump to directly receive or contact the expressed mammary fluid as it is pumped), or may be provided separately (for example as a non-integral membrane, filter, affinity column or blotting material to which mammary fluid or mammary fluid components are exposed to collect a biological sample for assay purposes).

In more detailed embodiments of the invention, kits include reagents and/or devices for detecting the presence and/or amount of a breast disease marker in the biological sample, for example an immunological or molecular probe that binds or reacts with a breast cancer marker. Among these possible reagents or devices are immunological and non-immunological probes for detecting the presence or amount of a breast cancer marker in the biological sample. The kits may also contain suitable buffers, preservatives such as protease inhibitors, direct or sandwich-type labels for labeling the probes, and/or developing reagents for detecting a signal from the label. In one aspect, kits of the present invention contain monoclonal antibodies useful for detecting and/or measuring a breast cancer marker in a sample. Such antibodies may be pre-labeled, or may be detected by binding to a secondary antibody optionally included in the kit. The antibody reagents may be provided in a separate container, or may be provided in combination in a series of containers. Within yet another aspect of the invention, kits contain sequence-specific oligonucleotide primers for detecting polynucleotide molecules encoding breast cancer marker proteins. Such primers may be provided in separate containers, or may be provided in combinations of one or more primer pairs in a series of containers. A broad selection of other kits are provided within the invention based on general knowledge in the art and on the description herein, including kits that contain specific instructions for carrying out the assays of the invention.

The following examples are offered by way of illustration, not by way of limitation.

EXAMPLE 1

Stimulation of Mammary Fluid Expression by Intranasal Administration of Oxytocin Coupled With Breast Pump Application Oxytocin nasal solution, acts specifically on the myoepithelial elements surrounding the alveoli of the breast and making up the walls of the lactiferous ducts, causing their smooth muscle fibers to contract and thus force any fluids present into the large ducts or sinuses where it can be expressed from the nipple by the further action of a breast pump. The nasal spray is promptly absorbed by the nasal mucosa to enter the systemic circulation. Intranasal application of the spray preparation is a practical and effective method of administration. Half-life of oxytocin in the human circulation is extremely short, approximately 10–15 minutes, and oxytocin is then rapidly removed from plasma by the kidney, liver, and mammary gland.

Because of the known effects of oxytocin to cause uterine contractions, pregnant women should not be treated by the methods contained herein unless the benefits of testing outweigh the risk of inducing premature labor.

The oxytocin nasal solution contains a concentration of natural or synthetic oxytocin, or a functional analog thereof, that is intranasally effective in a selected volume of administered spray to stimulate expression of mammary fluid from a nipple of the patient when a breast pump is applied to the nipple to assist mammary fluid expression. In the present example, a preferred oxytocin preparation containing approximately 40 USP units of oxytocin per ml of lactated Ringer's solution is administered into the nose with the squeeze bottle held in the upright position while the patient is in a sitting position. One or two sprays are administered into each nostril from a standard nasal squeeze bottle, which delivers approximately 0.5 ml of the oxytocin solution per spray in a fine mist when the bottle is squeezed. The number and volume of sprays administered, as well as the concentration of oxytocin in the solution, can be adjusted according to well known pharmacokinetic principles (See for example, Newton, *Ann. N.Y. Acad. Sci.* 652: 481–483; Mena, *Neuroendocrinology* 61: 722–730, 1995; Gonser, *Arch. Gynecol. Obstet.* 256: 63–66, 1995; Orhue, *Obstet. Gynecol.* 83: 229–233, 1994; Satin et al., *Am. J. Obstet. Gynecol.*, 166: 1260–1261, 1992; and Satin et al., *Obstet. Gynecol.* 83: 234–238, 1994, each incorporated herein by reference in its entirety) to ensure that the amount of oxytocin administered to the patient corresponds to an intranasally effective amount to stimulate the expression of at least 3 µl of mammary fluid in at least 50% of non-lactating female patients with the aid of the breast pump. For example, adjustments may be desired in the number of sprays delivered to the patient, and/or the timing of spray delivery, so that the clinician can modulate the dosage to each patient's varying sensitivity, and thereby minimize potential adverse side effects. In the present example, a preliminary dose of a single spray of the 40 Unit/ml oxytocin solution is delivered into each nostril of the patient, and the administering clinician waits for a short post-administration period of 2–3 minutes. After this period the breast pump is applied, and the clinician determines whether or not the amount of oxytocin delivered was sufficient to stimulate breast pump assisted expression of mammary fluid. If no fluid is expressed at this stage a booster dose of 1 or 2 additional sprays of the oxytocin solution is administered in each nostril, and the pump is reapplied after a 5–10 minute post-booster administration period.

After the intranasally effective dose of the oxytocin is administered and the clinician has allowed a suitable post-administration period to elapse for the oxytocin to reach and stimulate the target alveolar-ductal tissue, the breast pump is applied according to well known procedures. Negative pressures of 50–200 mm Hg are applied in the area of the nipple and are maintained, intermittently or continuously, for approximately 1–15 minutes, depending on the sensitivity of individual patients, oxytocin dosage and other factors. Alternatively, oxytocin can be administered by intramuscular or intravascular routes by well known means (Oxytocin Injection (synthetic), USP; Wyeth-Ayerst Laboratories) to effect the same response as intranasal administration.

Using the above methods, primary samples of mammary fluid containing at least 3 µl of fluid are expressed by 50% or more of non-lactating female patients. During or after the mammary fluid expression step, a biological sample is collected from the expressed mammary fluid. In the present example, a nitrocellulose filter is placed within the breast pump in line with a path of the expressed mammary fluid into the pump, so that the expressed fluid contacts the filter. Upon contact of the primary sample of expressed mammary fluid with the filter, cells, proteins and other desired components of the mammary fluid adhere to the filter to form a filter-bound biological sample for subsequent analysis. Other suitable biological samples, including whole mammary fluid samples, cytological samples of whole cells, membranes or other cellular components, and samples containing proteins, glycoproteins, peptides, nucleotides and other constituents of the primary mammary fluid sample can be collected with appropriate modifications of the above procedures, according to well known principles and methods.

EXAMPLE 2

Verification of Sample Origin and Quality Using Lysozyme Analysis

To ascertain that the primary sample of mammary fluid, or the collected sample, obtained by the above methods is of mammary origin and is not corrupted by likely contaminants, one or more constituents of normal mammary fluid are assayed for. In the present example, an enzyme that is ordinarily present in mammary fluid, lysozyme, is assayed in the primary mammary fluid sample to help confirm that the sample is of mammary origin. Lysozyme (muramidase) is an enzyme which hydrolyzes beta 1,4-glycosidic linkages in the mucopolysaccharide cell wall of a variety of microorganisms, which activity can be readily detected and quantified using a routine, inexpensive assay. In the present example, Lysozyme is measured in the primary mammary fluid sample using the Quantiplate Lysozyme Test kit (Kallestad, Chasta, Minn.). The assay employs the reagents and procedures provided by the manufacturer and specified in detail in the manufacturer's instructions, with the exception that a mammary fluid sample is substituted in place of serum, urine or tears. Analysis of these results establishes that the sample contains lysozyme, which is a normal component of human serum, urine, saliva, tears, nasal secretions, vaginal secretions, seminal fluid, and mammary fluid.

More specific assays are used in place of the lysozyme assay, or to supplement lysozyme assay results, particularly where clinical data for human patients are being gathered. Other mammary fluid markers for sample verification that are more specific than lysozyme can be readily incorporated within the invention, based on published and generally known information. In one example, the presence of cathepsin D is assayed using the monoclonal antibodies and methods disclosed in Vetvicka et al., *Biochem. Mol. Biol. Int'l.* 30: 921–928, 1993, incorporated herein by reference in its entirety). In another example, one or more human mammary epithelial antigens (HME-Ags) corresponding to glycoprotein components of the human milk fat globulin (HMFG) protein are detected in the primary mammary fluid sample, or in the biological sample that is used in the breast cancer marker assay, using specific antibody probes, as described by Rosner et al., *Cancer Invest.* 13: 573–582, 1995; Ceriani et al. *Proc. Natl. Acad. Sci. USA* 74: 582–586, 1982; Ceriani et al., *Breast Cancer Res. Treat.* 15; 161–174, 1990, each incorporated herein by reference in its entirety). In many cases, the sample verification assay can be incorporated within the breast cancer marker assay in a single procedure, for example as described below in Example 4, an assay for HME-Ags (wherein the HME-Ag findings are indicative of sample origin/quality, and also of the presence and/or quantity of a specific breast cancer marker in the sample). In another example, sample verification is achieved through a combinatorial (i.e. multiple marker) immunoassay targeting various cytokeratins, which can be detected as a panel of cytokeratins specifically expressed in mammary tissue sample. (See, Nagle, *J. Histochem. Cytochem.* 34: 869–881, 1986, incorporated herein by reference in its entirety). One or more of these cytokeratins (eg. K5, K8, K18 and K19) can be simultaneously or independently measured in the context of a breast cancer assay, and the level of expression of the subject cytokeratin(s) can yield information concerning the presence or status of breast cancer in a patient. (See for example, *Focus*, Harvard University News Office, Mar. 21, 1991, pp. 2–3; and Lee, *Proc. Natl. Acad. Sci.* 88: 1991, each incorporated herein by reference in its entirety).

EXAMPLE 3

Cytology in Biological Samples From Mammary Fluid

This example describes the use of conventional cytological techniques to identify and classify breast diseases from samples obtained as described in Example 1. Following collection of the sample in the sample collector, the central region of a clean glass microscopic slide is touched to the sample and a cover slip is slid over the sample to spread it along the surface of the slide. The slide is allowed to air dry and then is fixed, for examample in absolute alcohol and stained with standard cytological stains, such as methylene blue, hematoxylm and rosin, and other suitable stains.

The slides are then examined by light microscopy for evidence of atypical growth of cells and clumps of cells, using well known methods, including those described in "Diagnosis of Non-Palpable Breast Lesions: Ultrasonographically Controlled Fine-Needle Aspiration: Diagnostic and prognostic Implications of Cytology" by Jacqueline Mouriquand, published by S Karger Pub: July 1993, ISBN: 3805557477; "Breast: Guides to Clinical Aspiration Biopsy" by Tilde S. Kline, Irwin K. Kline, published by Igaku-Shoin Medical Pub: May 198g. LSBN: 0896401596; "Cytopathology ofthe Breast (Asop Theory and Practice of Cytopathology; 5)" by Shahla Masood, published by American Society of Clinical Pathology: November 199S, ISBN: 0891893806; "Fine Needle Aspiration Cytology and Its Clinical Applications: Breast and Lung" by Philip S. Feldman, published by American Society of Clinical Pathology: November 1984, ISBN: 0891891846, each incorporated herein by reference in its entirety.

EXAMPLE 4

Immunoassay for Human Mammary Epithelial Antigens in Biological Samples From Mammary Fluid Human mammary epithelial antigens (HME-Ags) are glycoprotein components of the human milkfat globule (HMFG) and of the membrane of the breast epithelial cell, which are released by breast tumors and not by normal breast tissue. (Ceriani et al., *Proc. Natl. Acad. Sci.* 74: 582–586, 1977, incorporated herein by reference in its entirety). In the present example, several HME-Ags, having molecular weights of 150, 70, and 45 kilodaltons, are detected and measured using specific anti-HMFG or anti-human mammary epithelial (α-HME) probes prepared and employed as described by Ceriani et al., *Proc. Natl. Acad. Sci.* 79: 5420–5425, 1982 (incorporated herein by reference in its entirety).

To begin the assay, biological samples from mammary fluid collected on nitrocellulose filters are eluted electrophoretically into phosphate buffered saline to provide a test sample, according to standard methods. Alternatively, whole mammary fluid or other types of biological samples obtained from mammary fluid can be constituted in an appropriate medium or mixture to provide a test sample for the assay. Once the test sample is thus provided, it is then assayed according to the HME-Ags radioimmunoassay (RIA) methods described in Ceriani et al., *Breast Cancer Res. Treat.* 15: 161–174, 1990 (incorporated herein by reference in its entirety).

Briefly, the RIA includes two preliminary treatments of the biological samples to separate interfering factors: a centrifugation step to separate out any fat present, and a second, precipitation step to precipitate potential immunocomplexes using polyethyleneglycol (PEG). The next steps comprise the assay proper, where HMFG antigen bound to a solid support (microtiter plates) is presented to stoichiometric or lesser amount of the α-HME antibody probe, and binding of the α-HME is competed by the biological samples from mammary fluid preliminarily treated as above. The amount of α-HME bound to HMFG antigen on the solid phase is determined in a final step by detection of the α-HME antibody probe by radioiodinated, affinity-purified rabbit anti-mouse immunoglobulin.

Solutions used in the assay are as follows: i) Phosphate buffered saline (PBS): 176 ml 0.05M $KH_2PO_4$, 608 ml 0.05M $Na_2HPO_4$, and 8 g NaCl brought up to 1000 ml in $H_2O$ (pH7.4). ii) RIA buffer: 0.1% BSA, in 0.3% Triton-X-100 (Research Prod. International Corp., Mount Prospect, Ill.) plus 0.05% sodium azide in PBS. iii) Detergent buffer: 0.3% Triton-X-100 plus 0.05% sodium azide in PBS. iv) Buffered polyethylene glycol (PEG): 6.6% PEG (M.W. 8000) (Sigma) plus 0.05% sodium azide in PBS) $^{125}$I-labeled affinity-purified rabbit anti-mouse immunoglobulin (Rα-mouse Ig) (Antibodies, Inc., Davis, Calif.), radioiodinated by the chloramine-T procedure as reported (Ceriani et al., *Proc. Natl. Acad. Sci.* 79: 5420–5425, 1982) and diluted to $4\times10^6$ cpm/ml, in RIA buffer. Rabbit polyclonal anti-HMFG antibodies or rabbit anti-human mammary epithelial antibodies (α-HME) were prepared and assayed as described (Id.).

To prepare a standard curve for evaluating assay results, control samples from normal human mammary fluid (exposed to nitrocellulose filters and eluted in the same manner as the nitrocellulose adsorbed, eluted test sample, or alternatively provided as normal whole mammary fluid or other selected type of sample obtained from normal mammary fluid, constituted in an appropriate medium or mixture to provide a suitable control assay sample) are centrifuged for 7 min at 10,240 rpm at 10° C. The upper white band formed at the top of the sample (if there is one) is discarded. Fresh 100 µg protein/ml solution of lyophilized dilipidated HMFG (Ceriani et al., *Proc. Natl. Acad. Sci.* 74: 582–586, 1977) in detergent buffer is prepared and sonicated at 10 second intervals for a total of 4 minutes (10 sec. of sonication, followed by a 10 sec. silent period) using a double step micro tip horn at 25 watts on a Sonifier Cell Disrupter 185 (Branson, Danbury, Conn.) at 4° C. HMFG solutions at concentrations of 0, 10, 33.3, 100, 333.3, and 1000 ng protein/ml are prepared in spun female sera, and 3 aliquots of 180 µl of each HMFG level in normal female sera are pipetted into 400 µl polyethylene microcentrifuge tubes (West Coast Sci. Emeryville, Calif.). 150 µl of 6.6% PEG solution is added to each microcentrifuge tube, and the tubes are incubated overnight on a rotating shaker at room temperature.

Test samples are processed in a comparable manner, by centrifuging 300–350 μl of the eluted nitrocellulose filtrate in solution (or, alternatively, of mammary fluid or other assay sample alternative) in a 400 μl microcentrifuge tube for 5–7 min. at 10,240 rpm at 10° C. The microcentrifuge tubes are then cut with a razor blade below the white band formed by the sera (if there was one) and 180 μl of remaining sera is transferred to a new microcentrifuge tube. 150 μl of a 6.6% PEG solution is then added to each microcentrifuge tube, and the tubes are incubated overnight on a rotating shaker at room temperature.

Day two (1) α-HME is diluted to its appropriate concentration in detergent buffer. The antibody solution has stoichiometric or lesser amounts of α-HME to 6 ng HMFG protein equivalent (prot. eq.). Six ng of HMFG is covalently bound to microtiter plates by the methylated BSA procedure previously described by Ceriani, In: Kennet et al., (eds) *Monoclonal Antibodies and Functional Cell Lines*, Plenum Press, New York, 1984, pp. 398–402, incorporated herein by reference in its entirety.

(2) To process test samples and control samples on the second day, microcentrifuge tubes are centrifuged for 7 min. at 10,240 rpm at 10° C. in a SHMT rotor with a Sorvall RC5C centrifuge. In triplicate, 55 μl of supernatant is pipetted into empty microtiter plate wells (Dynatech, Alexandria, Va.), and any precipitate pelleted is left undisturbed. 25 μl of 6.6% PEG solution is added to each well. 30 μl of α-HME diluted in detergent buffer is also added to each well, and a non-porous Scotch® tape is placed over the wells to avoid evaporation. The microtiter plate is then incubated overnight at room temperature on a rotary shaker.

Day Three (1) The microtiter plates are centrifuged (3000 r.p.m.) for 30 minutes at room temperature to decant suspended perceptible matter.

(2) 50 μl of RIA buffer is added to wells of microtiter plates containing 6 ng HMFG and aspirated off after 5 minutes.

(3) The total contents of microtiter plates from 1), save for any precipitation induced by the PEG and already pelleted, are carefully transferred to the wells of another set of microtiter plates containing 6 ng HMFG per well (Day 2,1), above.

(4) The microtiter plates are incubated for 3 hours with rotating agitation at room temperature.

(5) The plates are washed 5 times with RIA buffer using Dynadrop SR-1 automatic dispenser form Dynatech.

(6) 50 μl of the radioiodinated affinity-purified rabbit anti-mouse immunoglobulin diluted in RIA buffer is then adder per well.

(7) The plate is covered with tape and incubated with rotating agitation for 2 hours at room temperature.

(8) The plate is washed 5 times with RIA buffer.

(9) Wells are cut and counted in a gamma counter.

The results of these assays will yield important information concerning the presence and/or status of cancer in patients, comparable in scope and value to the data provided by serum assays conducted for the HME-Ag breast cancer marker by Ceriani et al., *Breast Cancer Res. Treat.* 15: 161–174, 1990. By selecting patient and control samples and developing and evaluating comparative data according to the procedures followed by Ceriani and his coworkers, the assay methods of the invention will also be readily adapted for use in direct clinical applications to determine both prognostic and treatment related variables in breast cancer patients. Reagents and conditions for the assays can of course be substituted or adjusted depending on a variety of anticipated variables, by applying well known immunological methods and principles.

EXAMPLE 5

Competitive Radioimmunoassay for Non-Penetrating Glycoprotein in Biological Samples From Mammary Fluid This competitive radioimmunoassay is based on the displacement by breast epithelial antigens contained in biological samples from mammary fluid obtained according to the methods of the invention of the binding of stoichiometric or lesser quantities of the monoclonal antibody Mc5 to a solid-phase-bound antigen known as non-penetrating glycoprotein (NPGP) contained in HMFG. HMFG is bound to a solid support and exposed to the Mc5 antibody during an incubation period allowing the antibody to bind the NPGP antigen in solid phase-bound HMFG. The presence and/or level of NPGP in the biological sample is ultimately examined by ability of the sample to compete for Mc5 binding to the NPGP antigen in the solid phase-bound HMFG, as detected and/or measured using a radiolabeled goat anti-mouse antibody to bind and label the Mc5 antibody probe.

Buffer and other solutions and reagents in this example are generally the same as those used for the HME-Ags polyclonal antibody radioimmunoassay described in Example 4, above. To provide test samples for the assay, biological samples from mammary fluid contained on nitrocellulose filters are eluted electrophoretically into phosphate buffered saline, according to standard methods. Alternatively, whole mammary fluid or other types of biological samples obtained from mammary fluid can be constituted in an appropriate medium or mixture to provide a test sample for the assay. Once the test sample is thus provided, it is then assayed according to the NPGP/Mc5 radioimmunoassay (RIA) methods described in Ceriani et al., *Breast Cancer Res. Treat.* 15: 161–174, 1990 (incorporated herein by reference in its entirety), as follows:

1) 400 μl of pooled normal female mammary fluid (exposed to nitrocellulose filters and eluted in the same manner as the nitrocellulose adsorbed, eluted test sample, or alternatively provided as normal whole mammary fluid or other types of biological samples obtained from normal mammary fluid constituted in an appropriate medium or mixture to provide a test sample) to provide a suitable control sample, which is diluted to 2.4 ml using RIA buffer at a 1:6 concentration.

2) A 500 μg/ml solution of lypholized HMFG is prepared in 1X PBS with 0.3% Triton-X-100, 0.05% sodium azide, and sonicated using a double step micro tip horn at 25 watts on a Sonifier Cell Disrupter 185 (Branson, Danbury, Conn.) for 4 minutes (10 sec. sonication, 10 sec. silent period, at 4° C.).

3) Solutions to prepare a standard curve are prepared using the 2.4 ml 1:6 normal female serum and increasing amounts of HMFG (0, 0.25, 2.5, 25, 50 μg/ml HMFG, as described above in Example 4).

4) Each test assay sample is diluted 1:6 with RIA buffer (40 μl of serum to 200 μl RIA buffer) to form a diluted test assay sample, and vortexed.

5) Mc5 stock solution is prepared so that it contains less than stoichiometric amounts of antibody to 100 ng protein/well of HMFG covalently bound to microtiter plates prepared as previously described by Ceriani, In: Kennet et al., (eds) *Monoclonal Antibodies and Functional Cell Lines*, Plenum Press, New York, 1984, pp. 398–402, incorporated herein by reference in its entirety 6) 200 µl RIA buffer are added to each well of 100 ng HMFG and then aspirated after 5 minutes.

7) To prepare a standard curve, 30 µl of HMFG standardizing solutions (as in 3 above) are added in quadruplicate to a 100 ng protein/well HMFG microtiter well.

8) 30 µl of diluted test assay sample (or, alternatively, of mammary fluid or other assay sample alternative) are added in triplicate to 100 ng/well HMFG microtiter wells.

9) To each well 20 µl of the Mc5 stock solution is added.

10) Microtiter plates are covered with nonporous Scotch® tape and incubated overnight at room temperature on a rotating agitator.

11) The next day the wells are aspirated and washed 5 times with RIA buffer.

12) To each well 50 µl of 200,000 cpm/50 µl $^{125}$I -goat anti-mouse antibody are dispensed. The wells are covered with nonporous tape and placed on a rotating agitator for 3 hours at room temperature.

13) Wells are washed 5 times with RIA buffer.

14) Each well is cut and the radioactivity is counted using a gamma counter.

The results of these assays will yield important information concerning the presence and/or status of cancer in patients, comparable in scope and value to the data provided by serum assays conducted for the NPGP breast cancer marker by Ceriani et al., *Breast Cancer Res. Treat.* 15: 161–174, 1990. By selecting patient and control samples and developing and evaluating data according to the well known procedures followed by Ceriani and his coworkers, the assay methods of the invention will be readily adapted for use in direct clinical applications to determine both prognostic and treatment related variables in breast cancer patients. As will be understood by those skilled in the art, reagents and conditions for the assays can be substituted or adjusted depending on a variety of anticipated variables, according to well known immunological methods and principles.

EXAMPLE 6

Solid Phase Immunoassay for Mucinous Carcinoma Associated Antigen in Mammary Fluid This example uses a sensitive, solid phase immunoassay to detect the mucinous carcinoma associated antigen (MCA) in biological samples from mammary fluid obtained according to the methods of the invention. MCA concentrations are determined using an antibody-bead immunoassay kit provided by Hoffman-La Roche (Basel, Switzerland), and using the reagents and procedures provided by the manufacturer and described in further detail in Eskelinen et al., *Anticancer Res.* 9: 437–440, 1989. Briefly, test assay samples of whole mammary fluid and standards are first incubated with MCA monoclonal antibody beads and then, after appropriate washings, enzyme (horseradish peroxidase) labeled secondary antibody is added. During the second incubation the anti-MCA enzyme conjugates are attached to the antibody antigen complex on the beads. Excess conjugates are removed by washing and, finally, enzyme substrate are added and the color formed is recorded.

The solid phase assay format presented in this example can be adapted for use in a wide array of other assays to detect and/or measure other cancer markers besides the MCA marker, with enhanced sensitivity. In addition, the results of these assays can be evaluated along with those of complementary assays detecting and/or measuring different markers to yield more precise information concerning the presence and/or status of cancer in patients, as exemplified by the combinatorial MCA/CA 15-3 assays described by Eskelinen et al., *Anticancer Res.* 9: 437–440, 1989; see also Eskelinen et al., *Anticancer Res.* 8: 665–668, 1988, each incorporated herein by reference in its entirety.

EXAMPLE 7

Western Analysis of Proteins From Cellular Fractions of Human Mammary Fluid Using Polyclonal and Monoclonal Antibody Probes to Detect Vasopressin A variety of assays are provided by the present invention that focus on cellular samples from human mammary fluid. In general, these assays rely on isolation by standard separation methods (eg. centrifugation, sucrose gradient, etc.) of cells, membranes or other cell components from whole mammary fluid expressed according to the above methods. Biological samples containing whole cells from expressed mammary fluid are particularly useful for cytological and cytochemical examination to detect and evaluate breast cancer in patients. Biological samples containing purified cell membrane fractions from human mammary fluid are particularly useful in this context, for example to detect and/or measure breast cancer markers that are expressed by alveolar-ductal cells as intracellular or membrane bound proteins and are therefore not as readily detected in liquid fractions of mammary fluid as secreted proteins.

The present example focuses on assays for detecting the peptide hormone vasopressin in biological samples from mammary fluid, using methods adapted from North et al., *Breast Cancer Res. Treat.* 34: 229–235, 1995. Specifically, this assay uses a test sample of crude protein isolated from a pooled sample of cells obtained from expressed mammary fluid. The cells are separated from whole mammary fluid according to standard methods, and crude protein is extracted from the cells by sonication in 100 volumes of 0.1M HCl. The resulting protein suspensions are then centrifuged at 1500×g for 10 min. at ambient temperature, and soluble protein is precipitated with 40% TCA. This protein is pelleted by centrifugation at 10,000×g for 2 min. TCA is then removed from pellets by washing (×2) with ether. Protein is resuspended in 0.1M Tris HCl (pH8.7), reduced with mercaptoethanol at 100° C. for 5 min. (and in some cases S-alkylated with N-ethyl maleimide), and subjected to SDS-PAGE electrophoresis on 15% gels at pH 9.3 using the method of Laemeli, *Nature* 227: 680–685, 1970, incorporated herein by reference in its entirety. Separated proteins are then electrophoretically transferred with 20 mM Tris glycine (pH 8.0) to Immobilon PVDF membranes (Millipore, Bedford, Mass.). These membranes are blocked with a 5% non-fat milk solution, washed (1×15 min., 2×5 min.) with PBS containing 0.5% Triton, and incubated with preparations of mouse monoclonal antibody to VP-HNP, with rabbit polyclonal antibodies to VP, with rabbit polyclonal antibodies to VAG, or with ubiquitous mouse or rabbit IgG (negative controls) (for description of antibodies and antibody preparation see North et al., *Breast Cancer Res. Treat.* 34: 229–235, 1995, incorporated herein by reference in its entirety), for 1 h at ambient temperature.

Following a second wash in PBS-Triton (1×15 minnn., 2×5 min.), the membranes are treated, respectively, with goat anti-mouse IgG-horseradish peroxidase conjugate or goat anti-rabbit IgG-horseradish peroxidase conjugate for 1 h, and then washed with PBS-Triton (1×15 min., 4×5 min.). Immunoreactive proteins are visualized using an ECL Western Blotting Detection System with exposure of x-ray film from 10 seconds to 5 min. Prestained SDS-PAGE standard proteins are employed as molecular size markers.

Recent studies suggest that vasopressin is universally expressed in breast carcinoma and is absent from normal breast cells. North et al., *Breast Cancer Res. Treat.* 34: 229–235, 1995. These and other results indicate that vasopressin and its relatives are important breast cancer markers which can be readily detected using immunological assays of proteins isolated from breast tumor cells. Accordingly, the results of the present example using cell samples isolated from human mammary fluid are also expected to yield important information concerning the presence and/or status of cancer in patients.

EXAMPLE 8

Quantification of Carcinoembryonic Antigen in Biological Samples From Mammary Fluid by Dot Immunoblotting Assay Among the more sensitive assays of the invention, useful for measuring low levels of breast cancer markers and for detecting markers when only small volumes of expressed mammary fluid are available, is the dot immunoblotting assay. In the present example, carcinoembryonic antigen (CEA) is measured in whole mammary fluid using an Elmotech anti-CEA monoclonal antibody kit (Mochid Pharmaceutical Co., Tokyo, Japan) in a dot blot assay format. Briefly, anti-CEA monoclonal antibody is diluted to appropriate concentrations and coated on the plastic film. Aliquots (5 μl) of either standard CEA solution (0, 100, 200, and 500 ng/ml), or of the whole mammary fluid assay sample, are smeared on the immobilized film. Assay standards are prepared from purified antigen preparations, in accordance with the Elmotec kit manufacturer's instructions. If necessary, 1000 ng/ml CEA solution is also used as a standard. After drying at room temperature, the film is exposed to peroxidase-conjugated anti-CEA antibody for 20 min at room temperature. The film is then washed extensively with 1M saline containing 0.5% (v/v) Tween 20. The enzyme reaction is visualized using tetramethylbenzidine as a chromogen. The developing solution consists of 0.05 mM tetramethylbenzidine and 0.01% hydrogen peroxide in McIlvain buffer (0.1% M phosphate-citrate buffer), pH 5.0, containing 10% methanol. The concentration of CEA in the mammary fluid assay sample is determined by comparing the color intensities with a corresponding standard.

The assay disclosed in the present example, and related assays incorporating antibodies to other tumor markers besides CEA, are particularly useful for measuring low levels of breast cancer markers and for detecting markers in limited sample volumes. The results of these assays will yield important information to determine both prognostic and treatment related variables in breast cancer patients. As will be understood by those skilled in the art, reagents and conditions for the assays can be substituted or adjusted depending on a variety of anticipated variables, according to well known immunological methods and principles.

EXAMPLE 9

Detection of Procathepsin D and Cathepsin D Activity in Biological Samples From Mammary Fluid Cathepsin D is a lysosomal aspartic proteinase which has been studied intensively as a marker for cancer processes necessary for metastasis. In the present example, polyclonal antibodies against procathepsin D are used to immunoprecipitate and immunochemically detect proteins from whole mammary fluid or cell lysates from mammary fluid, generally according to the methods disclosed in Vetvicka et al., *Biochem. Mol. Biol. Int'l.* 30: 921–928, 1993 (incorporated herein by reference in its entirety). Alternatively, or as a complementary assay, the protease activity of cathepsin D is detected, also according to the methods disclosed in Vetvicka et al. (Id.). Briefly, pooled whole mammary fluid (preferably 3 ml if available) is diluted with 3 ml of buffer A (50 mM Tris.HCl, 5 mM $CaCl_2$, 1 mM $MgCl_2$, 500 mM NaCl pH 7.2). The suspension is centrifuged for 30 minutes at 10,000 g. The resulting water phase is centrifuged again under the same conditions. The soluble part (total of approximately 4.5 ml) is loaded on a 1 ml column of Concanavalin A Sepharose (Pharmacia, Uppsala, Sweden) equilibrated in buffer A, and after washing with buffer A the retained proteins are eluted using 0.75M methyl α-D-mannopyranoside. The fractions (250 μl) are analyzed for cathepsin D activity using the $^{14}C$ hemoglobin assay as described by Lin et al., *J. Biol. Chem.* 264: 4482–4489, 1989 (incorporated herein by reference in its entirety), by western blots and by silver-stained electrophoresis. The inhibition of human milk procathepsin D is accomplished by adding 2 μl of 1 mM pepstatin A (Boehringer Manheim, Germany) dissolved in methanol to the reaction mixture.

This assay provides but one example of many possible embodiments of the invention that incorporate known biochemical assays, in addition to, or supplemental to immunological assays, to evaluate biological samples from mammary fluid to determine cancer related variables. The fundamental methods provided herein for obtaining samples from human mammary fluid render these assays readily adaptable for widespread clinical application to detect and/or measure the activity of a subject breast cancer marker within a non-invasive screening protocol.

Those with ordinary skill in the art will appreciate that other embodiments and variations of the invention are possible which employ the same inventive concepts described above. Most particularly, a wide and rapidly expanding array of useful breast cancer markers (including proteins, DNA and RNA sequences and other markers) and probes (including immunological, nucleotide and biochemical probes) are readily available for adaptation and use within the methods and kits of the invention. These markers and probes are described or referenced to a large extent in the literature cited and incorporated within the present disclosure, or are elsewhere published in the literature or well known in the art. Among these known and emerging markers and probes, useful examples within the invention include Her 2 (also known as erbB-2 and neu). Her 2 is a transmembrane glycoprotein growth factor receptor of the EGF receptor family encoded by a gene located on chromosome 17q, a region of frequent amplification in breast cancer cell lines. This marker is highly predictive of breast cancer and can be detected in cellular samples of the invention using known nucleotide probes to detect genetic defects in Her 2, or to detect and/or measure mRNA to determine overexpression of Her 2 linked to increased proliferation of cancer cells. (See for example, Visscher et al., In Weinstein and Graham (eds) *Advances in Pathology and Laboratory Medicine*, vol 5, St Louis, Mosby Yuear Book, 1992, pp. 123–161; Barbareschi et al., *Am. J. Clin. Pathol.* 98: 408–418, 1992; Slamon et al., *Science* 235: 177–182, 1987; each incorporated herein by reference in its entirety). Protein levels of Her 2 are also readily detected using available immunological probes. (For review see Porter-Jordan et al., *Hematol. Oncol. Clin. North Amer.* 8: 73–100, 1994 and articles cited on page 80 therein, each incorporated herein by reference in its entirety). Additional markers for use within the invention include EGF and the EGF receptor, for which immunological and non-immunological probes and assay methods readily adaptable within the invention are characterized in detail at page 80–81 of Porter-Jordan et al., *Hematol. Oncol. Clin. North Amer.* 8: 73–100, 1994 and in the references cited therein, each incorporated herein by reference in its entirety. Additional examples of proliferation markers, growth factors and receptors, proteases, adhesion factors, angiogenic factors, oncogenes and tumor suppressor genes that may provide useful breast cancer markers and probes within the methods and kits of the invention include Ki67 Growth Factor, Cyclin D1, Proliferating Cell Nuclear Antigen, Transforming Growth Factor α, Tissue Plasminogen Activator, Insulin Growth Factor Receptors, Collagenase Type IV, Laminin Receptor, Integrins, p53, rb, nm23, ras, c-myc, Heat Shock Proteins, Prolactin, Neuron-Specific Enolase, IR-14, KA 1, KA 14, Alpha-Lactalbumin, Actin, and many others, the majority of which are described along with available immunological and non-immunological probes and assay methods readily adaptable within the invention in the review by Porter-Jordan et al., *Hematol. Oncol. Clin. North Amer.* 8: 73–100, 1994 and in the references cited therein, each incorporated herein by reference in its entirety. Adaptation of these markers and probes within the invention can be readily accomplished based on the teachings provided herein and in the cited references, supplemented by general knowledge in the art. Therefore, the invention is not to be limited by the above description, but is to be determined in scope by the claims which follow.

I claim:

1. A non-invasive method for obtaining a biological sample from a mammary organ of a patient, comprising the steps of:
    administering to the patient an effective amount of a natural or synthetic oxytocin to stimulate expression of mammary fluid from a nipple of the patient;
    applying a breast pump to the nipple; and
    collecting a biological sample by exposing the expressed mammary fluid to a solid phase medium removably placed within said breast pump to retain a breast disease marker from the expressed mammary fluid.

2. The method for obtaining the biological sample according to claim 1, wherein the natural or synthetic oxytocin is administered by one or more modes of administration selected from the group consisting of intranasal administration, intravascular administration and intramuscular administration.

3. The method for obtaining the biological sample according to claim 1, wherein the natural or synthetic oxytocin is administered by intranasal administration.

4. The method for obtaining the biological sample according to claim 1, wherein the solid phase medium is selected from the group consisting of microscopic slides, membranes, filters and beads.

5. The method for obtaining the biological sample according to claim 1, wherein the step of administering involves administering an intranasal spray containing 40 USP units of oxytocin per ml in a liquid carrier.

6. The method for obtaining the biological sample according to claim 1, wherein the biological sample is selected from the group consisting of whole mammary fluid, whole cells, cell fragments, cell membranes, proteins, glycoproteins, peptides and nucleotide components of a primary mammary fluid sample.

7. The method for obtaining the biological sample according to claim 1, wherein the solid phase medium is a nitrocellulose filter.

8. An assay method for determining the presence or amount of a breast disease marker in a biological sample obtained from a mammary organ of a patient, comprising the steps of:
    administering to the patient an effective amount of a natural or synthetic oxytocin to stimulate expression of mammary fluid from a nipple of the patient;
    applying a sample collector to the nipple; and
    applying a breast pump to the nipple; and
    collecting a biological sample by exposing the expressed mammary fluid to a solid phase medium removably placed within said breast pump to retain a breast disease marker from the expressed mammary fluid;
    detecting the presence or amount of a breast disease marker in the biological sample.

9. The assay method according to claim 8, wherein the breast disease marker is a breast cancer marker.

10. The assay method according to claim 8, wherein the natural or synthetic oxytocin is administered by one or more modes of administration selected from the group consisting of intranasal administration, intravascular administration and intramuscular administration.

11. The assay method according to claim 8, wherein the natural or synthetic oxytocin is administered by intranasal administration.

12. The assay method according to claim 8, wherein the solid phase medium is selected from the group consisting of microscopic slides, membranes, filters and beads.

13. The assay method according to claim 8, wherein the step of administering oxytocin involves administering an intranasal spray containing 40 USP units of oxytocin per ml in a liquid carrier.

14. The assay method according to claim 8, wherein the biological sample is selected from the group consisting of whole mammary fluid, whole cells, cell fragments, cell membranes, purified proteins, bulk proteins, glycoproteins, peptides and nucleotide components of a primary mammary fluid sample.

15. The assay method according to claim 8, wherein the breast disease marker is selected from the group consisting of a protein, a peptide, a glycoprotein, a lipid, a DNA polynucleotide and an RNA polynucleotide.

16. The assay method according to claim 8, wherein the breast disease marker is detected by employing an immunological probe that specifically binds the marker.

17. The assay method according to claim 16, wherein the immunological probe is a monoclonal antibody.

18. The assay method according to claim 8, wherein the breast disease marker comprises a cytological phenotype of cells, cell clusters or cell fragments.

19. The assay method according to claim 8, wherein a plurality of different breast disease markers are detected using a panel of immunological probes.

20. The assay method according to claim 8, wherein the breast disease marker is a breast cancer marker selected from the group consisting of a DNA polynucleotide and an RNA polynucleotide, and wherein the step of detecting the presence or amount of the breast cancer marker in the biological sample employs a nucleotide probe.

21. The assay method according to claim 8, wherein the breast disease marker is selected from the group consisting of Ki67 Growth Factor, Cyclin D1, Proliferating Cell Nuclear Antigen, Transforming Growth Factor α, Tissue Plasminogen Activator, Insulin Growth Factor Receptors, Collagenase Type IV, Laminin Receptor, Integrins, p53, rb, nm23, ras, c-myc, Heat Shock Proteins, Prolactin, Neuron-Specific Enolase, IR-14, KA 1, KA 14, Alpha-Lactalbumin and Actin.

22. The assay method according to claim 8, wherein the breast disease marker is selected from the group consisting of CEA, HMFG, MCA, vasopressin and cathepsin D.

23. The assay method according to claim 8, wherein the solid phase medium is a nitrocellulose filter.

24. A kit for determining the presence or amount of a breast disease marker in a biological sample obtained from a mammary organ of a patient, comprising:
   a pharmaceutical preparation of a natural or synthetic oxytocin in a biologically suitable carrier;
   collecting means for collecting a biological sample from expressed mammary fluid, said collecting means comprising a solid phase device selected from the group consisting of microscopic slides, membranes, filters and beads; and
   detecting means for detecting the presence and/or amount of a breast disease marker in said biological sample.

25. The kit according to claim 24, wherein the oxytocin preparation is provided in an intranasal spray applicator and contains approximately 40 USP units of oxytocin per ml of a liquid carrier.

26. The kit according to claim 24, wherein the collecting means is fluidly connected to a breast pump applicable to a human breast and designed to generate sustained negative pressures in an area surrounding a nipple of between about 50–200 mm Hg.

27. The kit according to claim 26, wherein the collecting means is incorporated within the breast pump.

28. The kit according to claim 24, wherein the detecting means includes an immunological probe that specifically binds the breast disease marker.

29. The kit according to claim 28, wherein the immunological probe is a monoclonal antibody.

30. The kit according to claim 24, wherein the detecting means includes a panel of immunological probes that collectively bind to a plurality of different breast disease markers.

31. The kit according to claim 24, wherein the detecting means includes a nucleotide probe that specifically hybridizes to a breast disease marker selected from the group consisting of a DNA polynucleotide and an RNA polynucleotide.

32. The kit according to claim 24, wherein the detecting means includes an immunological probe that specifically binds to one or more breast cancer markers selected from the group consisting of Ki67 Growth Factor, Cyclin D1, Proliferating Cell Nuclear Antigen, Transforming Growth Factor α, Tissue Plasminogen Activator, Insulin Growth Factor Receptors, Collagenase Type IV, Laminin Receptor, Integrins, p53, rb, nm23, ras, c-myc, Heat Shock Proteins, Prolactin, Neuron-Specific Enolase, IR-14, KA 1, KA 14, Alpha-Lactalbumin and Actin.

33. The kit according to claim 24, wherein the detecting means includes an immunological probe that specifically binds to one or more breast cancer markers selected from the group consisting of CEA, HMFG, MCA, vasopressin and cathepsin D.

34. A kit for collecting a biological sample from a mammary organ of a patient, comprising:
   a breast pump; and
   a solid phase sample collection medium selected from the group consisting of membranes, filters and beads for placement in fluid connection with said breast pump to contact the biological sample and retain a breast cancer marker.

35. The kit according to claim 34, wherein the solid phase sample collection medium is a nitrocellulose filter.

36. The kit of claim 34, wherein the solid phase sample collection medium is incorporated within the breast pump.

37. The kit of claim 34, wherein the solid phase sample collection medium is removably placed within the breast pump.

\* \* \* \* \*